United States Patent [19]
Yuda et al.

[11] Patent Number: 5,217,449
[45] Date of Patent: Jun. 8, 1993

[54] MEDICAL CAPSULE AND APPARATUS FOR ACTIVATING THE SAME

[75] Inventors: Shunichi Yuda; Hiroshi Ito; Mamoru Tanaka, all of Hanishina, Japan

[73] Assignee: Miyarisan Kabushiki Kaisha, Nagano, Japan

[21] Appl. No.: 625,911

[22] Filed: Dec. 11, 1990

[51] Int. Cl.⁵ .............................................. A61K 9/22
[52] U.S. Cl. ................................... 604/890.1; 604/131
[58] Field of Search ................. 604/93, 118, 121, 131, 604/132, 135, 244, 296, 256, 890.1–891.1

[56] References Cited

U.S. PATENT DOCUMENTS

| | | | |
|---|---|---|---|
| 3,659,600 | 5/1972 | Merrill | 604/131 |
| 4,239,040 | 12/1980 | Hosoya et al. | 604/135 |
| 4,425,117 | 1/1984 | Hugemann et al. | 604/890.1 |
| 4,507,115 | 3/1985 | Kambara et al. | 604/93 |

*Primary Examiner*—Max Hindenburg

*Attorney, Agent, or Firm*—Mathews, Woodbridge & Collins

[57] ABSTRACT

A medical capsule having an outer cylinder and a piston movable in the outer cylinder, the piston being activated by an externally given signal so as to discharge a medicine to the outside of the capsule or to suck a humor for a sampling purpose, as well as an apparatus for activating this medical capsule. The capsule has a remote-controllable means including a normally-opened lead switch which connects a power supply to an activating means in response to an externally given magnetic signal thereby initiating activation of the medical capsule, whereby a simple medical capsule which is operative with minimized electrical power consumption without affecting the living body can be obtained. The activating apparatus has a pair of magnetic field generating units arranged side-by-side so as to generate magnetic lines of force in various directions and to form magnetic fields covering a large area, thus ensuring correct activation of the medical capsule inside the living body.

9 Claims, 6 Drawing Sheets

MEDICAL CAPSULE AND APPARATUS FOR ACTIVATING THE SAME

BACKGROUND OF THE INVENTION

1. Field of the Invention

The present invention relates to a medical capsule for conducting sampling of a humor or dosage of a medicine at a desired location inside a living body. The present invention also is concerned with an apparatus for activating such a medical capsule from the outside of the living body.

2. Description of the Prior Art

Hitherto, a medical capsule has been known as a device which conducts sampling of, for example, intestinal liquid, or dosage of a medicine at a predetermined location in a living body, for the purpose of diagnosis or medical treatment.

The medical capsule has a capsule-like hermetic casing having an openable portion. When such a medical capsule swallowed by a patient has reached a predetermined position inside the patient's body, the openable portion is opened so as to sample a humor such as a gastric juice or to dose a medicine charged in the capsule. Then, the capsule is discharged through anus of the patient and collected. Such a medical capsule is disclosed, for example, in Japanese Patent Publication Nos. 53-53182, 55-9033. 55-49853, 57-1255, 57-39776 and 61-11104.

This medical capsule is very small and can easily swallow without any pain and, hence, is attracting attention in the medical fields. In particular, the medical capsule, when used for the purpose of dosage, can directly dose the medicine to the affected part of the body, thus attaining a great medical treating effect. For instance, when this capsule is used against a cancer in an alimentary system, a remarkable carcinostatic effect without side-effect, thus offering a desired treating effect.

A known medical capsule for sampling will be described in more detail. As shown in FIG. 10, a medical capsule used for the sampling purpose has a hermetic casing 103 composed of a frame 101 and an outer cylinder 102. A piston 104 is movably received in the outer cylinder 102. As the piston 104 is moved, a vacuum region is produced in the outer cylinder 102 so that a gastric juice around the casing is sucked into the capsule through ports 105, 106, whereby the sampling of the gastric juice is conducted. This medical capsule for sampling is disclosed in Japanese Utility Model Publication No. 57-57684.

The piston 104 in this medical capsule operates by the springing force of a spring 107. Initially, the spring 107 is compressed and held in the compressed state by a fixing thread 108. After the capsule is swallowed by a patient, the position of the capsule is traced and monitored by an external monitoring device such as a roentgen apparatus. When the capsule has reached a predetermined position inside the body, a resonance of a resonance circuit is caused by an externally given radio wave so as to supply an electrical current to a filament 109. The fixing thread 108 is then molten by the heat generated by the filament 109 so that the piston 104 is projected by the resilient force of the spring 107, whereby the capsule sucks a gastric juice to complete the sampling.

FIG. 11 illustrates a known medical capsule used for the purpose of dosage. This capsule has a medicine chamber 110 in one end of which a piston 104 is received slidably, whereas a discharge port 112 formed in the other end of the medicine chamber 110 is normally closed by a plug 111. This medical capsule is disclosed, for example, in Japanese Patent Publication No. 55-49853. Other portions are materially the same as those of the medical capsule shown in FIG. 10. For information, the same reference numerals are used to denote the same parts as those appearing in FIG. 10 and the description of such parts is omitted herein.

In operation, the fixing thread 108 is cut by the same method as that described before, so that the piston 104 moves inside the outer cylinder 102 so that the medicine Y in the medicine chamber is pressurized to forcibly remove the plug 111 so as to be discharged from the capsule.

Various other methods have been proposed for externally activating medical capsules. For instance, the following four methods have been proposed.

(1) Direct Remote Control Method

Long electric cords are connected to the capsule and the ends of the cords are held outside the body after the capsule is swallowed. When the capsule has reached a desired position, electrical current is supplied from an external power supply to the capsule through the cords so as to cut the fixing thread. Thus, the fixing thread is cut directly by a remote control.

(2) Melting method

This method eliminates the necessity for external monitoring apparatus and external power supply. Namely, a portion of the hermetic casing is formed of a digestive film which can be molten by a predetermined environment inside the body. A cutter for cutting the thread is operated as this digestive film is molten. This method is disclosed in Japanese Patent Publication No. 55-30385.

(3) Vibration Method

A vibrator element inside the capsule is vibrated by an externally given vibratory energy so as to mechanically cut the fixing thread. This method is disclosed in Japanese Patent Publication No. 55-30386.

(4) Supersonic Method

In this method, a heater is energized by an externally applied supersonic wave so as to cut the fixing thread. This method is disclosed in Japanese Patent Publication No. 57-2015.

The term "medicine" in this specification is used to mean medical agents, microorganisms and so forth which are used for the purpose of diagnosis, curing, treatment and prophylaxis. The term "dosage" means application or dosage of such a medicine.

The following problem is encountered with the medical capsule of the type which supplies electrical current to a filament by a resonance circuit operated by an external instruction radio wave. Namely, in this type of medical capsule, an electrical current is continuously supplied even when the capsule is not being used once the capsule is assembled, in order to make sure of the safe operation of the capsule, and the switching of the circuit is conducted by means of a transistor. Consequently, the battery power is consumed heavily. In addition, a capsule which has been shelved long may fail to operate due to exhaustion of the battery. Furthermore, the effective reach of the radio wave, i.e., the distance within which the capsule can be operated without fail by the radio wave, differs according to individual patient. Usually, the effective reach of the radio wave is set to be 6 to 10 cm. The capsule therefore may not operate when applied to a fatty patient.

The direct remote control method also involves a problem in that it causes a physical pain on the patient because the patient is obliged to swallow not only the capsule but also electric cords connected thereto. From this point of view, indirect activating methods are preferred. Indirect activating methods, however, are also disadvantageous in that uncertain time lag tends to be caused between the moment at which the external activating apparatus is operated and the moment at which capsule is actually activated.

The medical capsule of digest type also contains a difficulty in that the control of position inside the body at which the capsule is activated is very difficult to conduct. The position varies according to the individual patients so that the discharge of the medicine cannot be controlled accurately.

The medical capsule of the vibration type also is defective due to inaccurate cutting of the fixing thread, thus impairing reliability of the dosage. In addition, this type of medical capsule has a complicated construction which makes it difficult to reduce the size and cost.

Furthermore, in known medical capsules of the type employing a closure plug, it is necessary that the closure plug securely holds the sealing condition when the capsule is not activated, whereas, when the capsule is activated, the plug 111 opens the discharge opening without fail and yet still held on the capsule without being severed therefrom. Consequently, a complicated connecting construction is required for connecting the plug 111 to the outer cylinder 102. In addition, the discharge of the medicine Y cannot be conducted with a high degree of reliability.

The fixing thread 108, which is used in the known medical capsule, is usually a cotton thread or a thread produced from synthetic fibers. Such a thread cannot be cut instantaneously. Namely, there is a slight time lag or delay until the fixing thread is cut. Such a delay makes it difficult to accurately control the position at which the capsule is activated, with the result that the expected curing or treating effect cannot be attained or the accuracy of examination is impaired due to inferior sampling.

SUMMARY OF THE INVENTION

Accordingly, a first object of the present invention is to provide a medical capsule which can operate with reduced power consumption and which can be shelved for a long time and yet capable of operating without fail for dosage or sampling while minimizing pain posed on the patient, thereby overcoming the above-described problems of the prior art.

A second object of the present invention is to provide an apparatus for activating a medical capsule, which has a long effective distance for activation and which can be operated easily with a high degree of reliability.

A third object of the present invention is to provide a fixing thread which can be cut easily when the capsule is used.

To achieve the first object, the invention provides a medical capsule including: a main block: an outer cylinder and a cover which are secured to both ends of the main block: a working chamber defined between the main block and the outer cylinder: a piston slidably received in the working chamber; a spring member acting between the piston and the main block so as to urge the piston towards the outer end of the outer cylinder; a fixing thread for fixing said piston to the main block against the force of the spring member; a filament for heating and melt-cutting the fixing thread: a battery for supplying electrical power to the filament; and a remote-controllable means capable of connecting the filament to the battery: wherein the improvement comprises: a medicine discharge opening formed in one end of the outer cylinder; a seal film closing the discharge opening so as to seal the working chamber; and a projection provided on the end of the piston 5 adjacent to the seal film so as to puncture the seal film when the piston advances.

To achieve the first object, the present invention also provides a medical capsule of the type described above, wherein the working chamber is a hollow chamber and is provided with a port through which a humor is sucked into the working chamber as a negative pressure is established in the working chamber as a result of the movement of the piston.

To achieve the first object, the present invention also provides a medical capsule of the type described above, wherein the remote-controllable means includes a by an externally applied magnetic force.

Preferably, the seal film is made of polytetrafluoroethylene.

To achieve the second object, the present invention provides an apparatus for activating a medical capsule which is placed at a predetermined position in a living body for the purpose of discharging a medicine or sampling a liquid inside the living body, the apparatus comprising: a pair of magnetic field generating units each containing a coil; and a current control unit for supplying the coil with a D.C. current.

To achieve the third object, the present invention provides a medical capsule, wherein a combustible material is applied to the fixing thread.

When the medical capsule of the present invention is used, the position of the swallowed capsule in the patient's body is monitored from the exterior and, when the capsule has reached a predetermined position, an activating signal is applied externally so as to instantaneously cut the thread. In consequence, the piston is made to slide in the working chamber so that a projecting portion of the piston breaks the seal film so that whole of the medicine charged in the working chamber is discharged without fail.

The medical capsule of the present invention, regardless of whether it is used for dosing or sampling purpose, may include a magnetically operable lead switch as control means. Such a lead switch can be turned on easily and without fail by an external magnetic flux generator. It is therefore possible to activate the capsule at a desired position without fail. Furthermore, since the effective distance of activation can be increased, the medical capsule can be shelved for a longer time with reduced consumption of the battery power. In addition, any unfavorable effect is eliminated and the construction is simplified.

According to the present invention, D.C. current after rectification by a current control section is supplied to a coil accommodated in each magnetic field generating member, so that a magnetic field is generated around each magnetic field generating member. According to the invention, since two such magnetic field generating members are arranged side-by-side so that a magnetic field is generated also in the space between both magnetic field generating members. Consequently, magnetic lines of force of many directions, as well as a magnetic field of a wide range, can be obtained, so that the capsule can be activated without fail when the body of the patient is brought to a position where the medical capsule falls within the region of the magnetic fields described above.

The fixing thread may be impregnated with a combustible material. When the filament is energized, the fixing thread is molten by the heat generated by the filament and by the heat produced by burning of the combustible material ignited by the heat generated by the filament. Consequently, the fixing thread can be cut almost instantaneously. Consequently, the operation of the piston can be effected without substantial delay after the operation of the external activating apparatus, thus enhancing the accuracy of the control of the capsule. The medical capsule of this type is used in a living body in which oxygen concentration is usually small. It is therefore preferred that the fixing thread is disposed in the cavity of the main block in contact with the filament, so that the melt-cutting of the fixing thread is promoted by burning of the combustible material by virtue of a certain amount of the oxygen contained in this cavity. The strength of the fixing thread itself is enhanced when the impregnating material is a combustible oil, whereby two incompatible requirements, i.e., ease of cutting of the thread and stability of fixing of the piston, are simultaneously satisfied.

DESCRIPTION OF THE PREFERRED EMBODIMENTS

Figure 1:
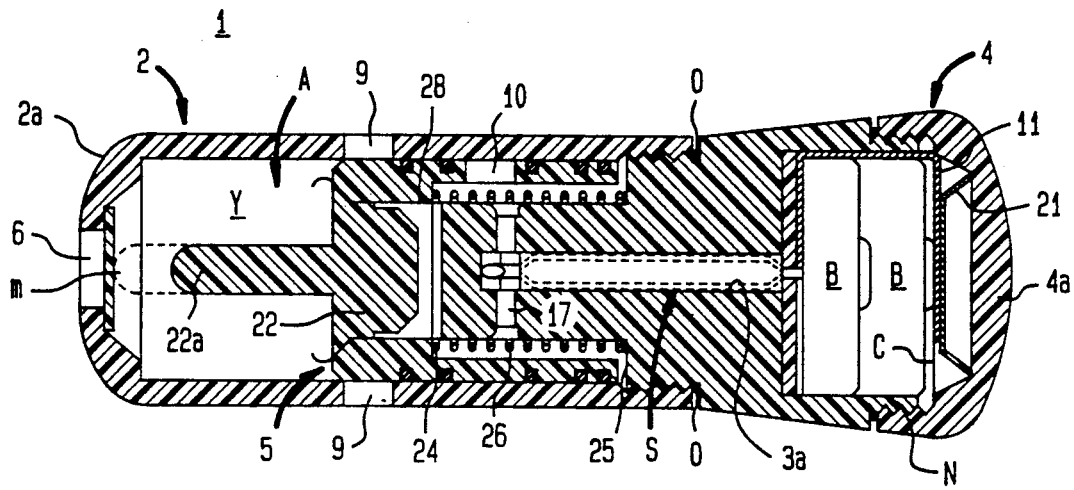
FIG. 1 is a sectional view of a first embodiment of the medical capsule in accordance with the present invention.

FIG. 1 shows a first embodiment of the medical capsule of the present invention intended for use in dosage of a medicine. The medical capsule of this embodiment has a generally elongated oval shape having a main block 3, an outer cylinder 2 made of polycarbonate and having a bottom-equipped cylindrical form, and a cover member 4, the outer cylinder 2 and the cover 4 being screwed to both ends of the main block 3 through intermediaries of "O" rings. A working chamber A is formed between the main block 3 and the outer cylinder 2. A piston 5 disposed in the working chamber A is urged towards the end of the outer cylinder 2 by means of the coiled spring 26 which acts between the piston 5 and the main block 3. A medicine chamber Y which is to be charged with a medicine is defined by the piston 5 and the outer cylinder 2.

Typical examples of the medicine charged in the medicine chamber Y are antibiotics formed from the following agents: antitherioma agents such as defcal (commercial name futrahool, produced by Taiho Yakuhin K. K.), anti-therioma agents (commercial name Picibanil, produced by Chugai Seiyaku K. K.), and Kawaratake-extract polysaccharide (commercial name Kurestin, produced by Kureha kagaku, K. K.); radioactive medicines such as sodium (commercial name Tekunesin Tc-99 produced by Medifix K. K.); sefem type medicines such as Sefarexin (commercial name Kefral, produced by Shionogi Seiyaku K. K.) and sefalexin (commercial name Keflex, produced by Shionogi Seiyaku K. K.); and synthetic penicillin type medicines such as sodium kuroxacillin (commercial name Orben, produced by Shionogi Seiyaku K. K.).

The outer cylinder 2 and the cover 4 respectively have dome-shaped bottoms 2a and 4a which enable the capsule to smoothly move in the patient's body. The bottom 2a of the outer cylinder 2 is provided with a medicine discharge port 6 which is usually covered with a seal film m. Preferably, the seal film m is made of a thin film of a material having a high resistance to medical liquid and easy to break, such as polytetrafluoroethylene. This, however, is only illustrative and the seal film m may be formed from other types of material.

Preferably, the outer cylinder 2 is provided with ports 9 formed substantially in the center of the side walls thereof. It is also preferred that ports 10 are formed in an intermediate portion of the piston 5. In operation, humor is introduced to the back side of the piston 5 through the ports 9 and 10 so as to negate any negative pressure behind the piston 5, thus ensuring smooth operation of the piston 5.

When pickup of the humor is to be avoided, these ports 9, 10 are omitted and, instead, compressed air is charged in a battery chamber C inside the cover 4. In such a case, the thread portion N where the cover 4 is screwed to the main block 3 has a substantial length so that air initially confined in the battery chamber C is progressively compressed as the cover 4 is screwed to the main block 3.

Figure 2:
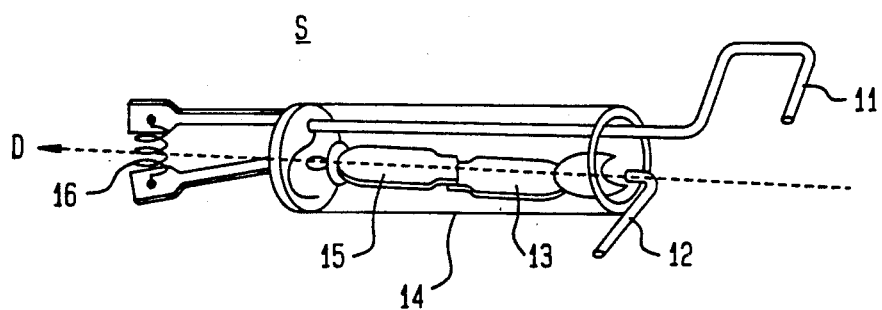
FIG. 2 is a perspective view of a lead switch incorporated in the first embodiment.

The main block 3 also is made of polycarbonate. The main block 3 is provided at its right end with a recess for accommodating a battery B and at its center with a central bore 3a which receives a lead switch s. The lead switch s is a normally-opened switch having two lead lines 11, 12 connected to a pair of silver batteries B, (each being of 1.5 V) as shown in FIG. 2. Lead line 12 has one end connected to a contact 13 which is received in a glass tube 14 so as not to unintentionally contact with the other contact 15. The contact 15 and the lead line 11 are extended externally of the glass tube 14 and are connected to each other through a filament 16. The contacts 13 and 15 are resilient magnetic members and are highly sensitive to magnetic lines of force of a direction of an arrow D so as to be turned on in response to this magnetic lines of force, thereby allowing electrical power to be supplied from the batteries B to the filament 16 to generate heat. When no magnetic force is applied, these contacts are kept off, i.e., away from each other, due to their resiliency.

In the drawings, numeral 21 designates a spring for pressing the battery B.

The piston 5 is a cylindrical member made of polycarbonate and adapted to slide within the outer cylinder 2. A thread retaining cap 22 is detachably press-fitted in the end of the outer cylinder 2. A projection 22a for puncturing or piercing the seal film m is provided on the end of the cap 22. A coiled spring 26 is loaded between a step 24 formed on the inner peripheral surface of the piston 5 and a step 25 formed on the main block 3.

The piston 5 is fixed to the main block 3 by a fixing thread 28 against the force of the coiled spring 26. Although not exclusive, the fixing thread 28 is made of a material having a high strength and a comparatively low melting point, e.g., a nylon thread having a melting point ranging between 200° C. and 270° C.

The fixing thread 28 has both ends fastened to the thread retaining cap 22 and is extended so as to contact with the filament 16 within a bore-like chamber 17 of a predetermined volume formed in the main block 3.

Preferably, a combustible material is applied to the fixing thread 28. The combustible material is preferably a non-volatile substance having a comparatively low flash point. Practical examples of the combustible material are wax, benzene, naphthalene and so forth, as well as combustible oil. The combustible material applied to the fixing thread 28 is easily ignited to promote the rupture of the fixing thread 28 by melting. When an oil is used as the combustible material, the mechanical strength of the fixing thread is increased, so that two generally incompatible requirements, i.e., ease of rupture and stability of support of the piston, are satisfied simultaneously.

Figure 4:
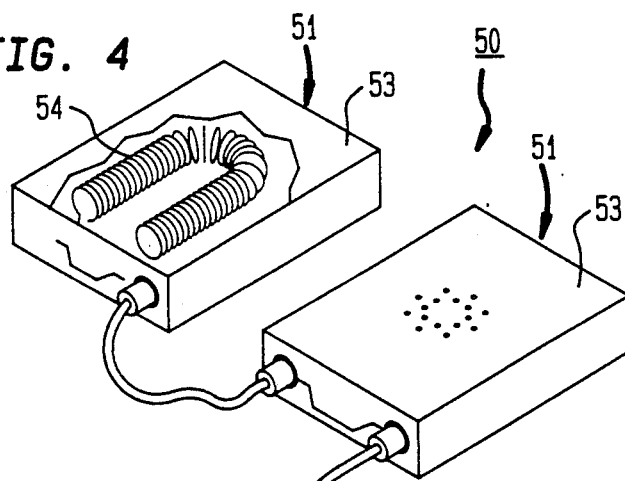
FIG. 4 is a schematic illustration of an embodiment of the activating apparatus for activating the medical capsule.
Figure 4:
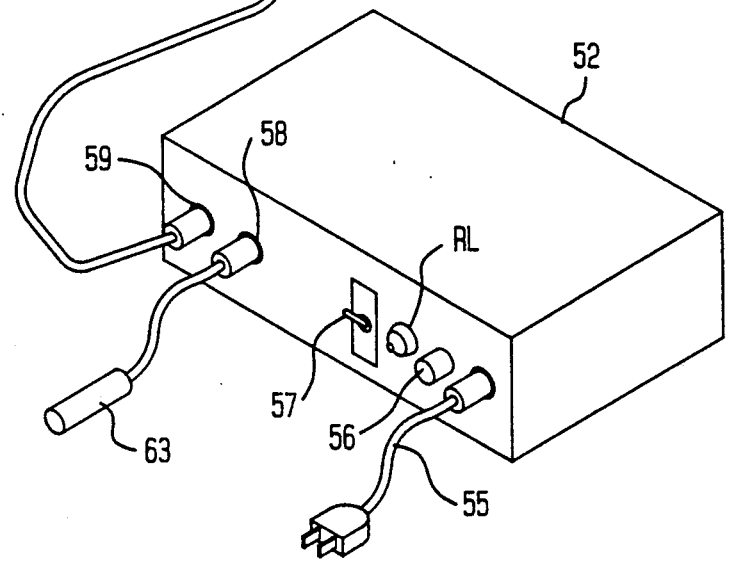

FIG. 4 illustrates an activating apparatus for activating the medical capsule described hereinbefore. The actuating apparatus 50 has magnetic field generating units 51, for magnetically turning on and off the contacts 13, 14 of the lead switch s, and a current control unit 52 through which electrical current is supplied to the magnetic field generating units 51.

Each of the magnetic field generating unit 51 has a box 53 in which is disposed a coil 54 formed by winding the lead line. In the illustrated embodiment, the coil is arranged substantially circularly so as to increase the number of the turns thereby intensifying the magnetic field, while improving the space factor, thus attaining a compact construction of the magnetic field generating unit 51. The configuration of the coil 54 in the illustrated embodiment, however, is only illustrative and the coil may be arranged linearly or in a semi-circular form.

As shown in FIG. 4, the box 53 of the magnetic field generating unit 51 also receives a fan F for cooling the coil which generates heat when supplied with electric current.

The current control unit 52 has a case on which are disposed a plug 55 through which A.C. 100 V power is supplied, a fuse 56 for the main circuit, a start lamp RL, a start snap switch 57, a connector 58 for connection to an operation switch, and D.C. power supply connector 59. The case encases a rectifier 60 for converting A.C. power into D.C. power and a buzzer BZ for informing the operator or the patient of the state of generation of the magnetic field.

Figure 5:
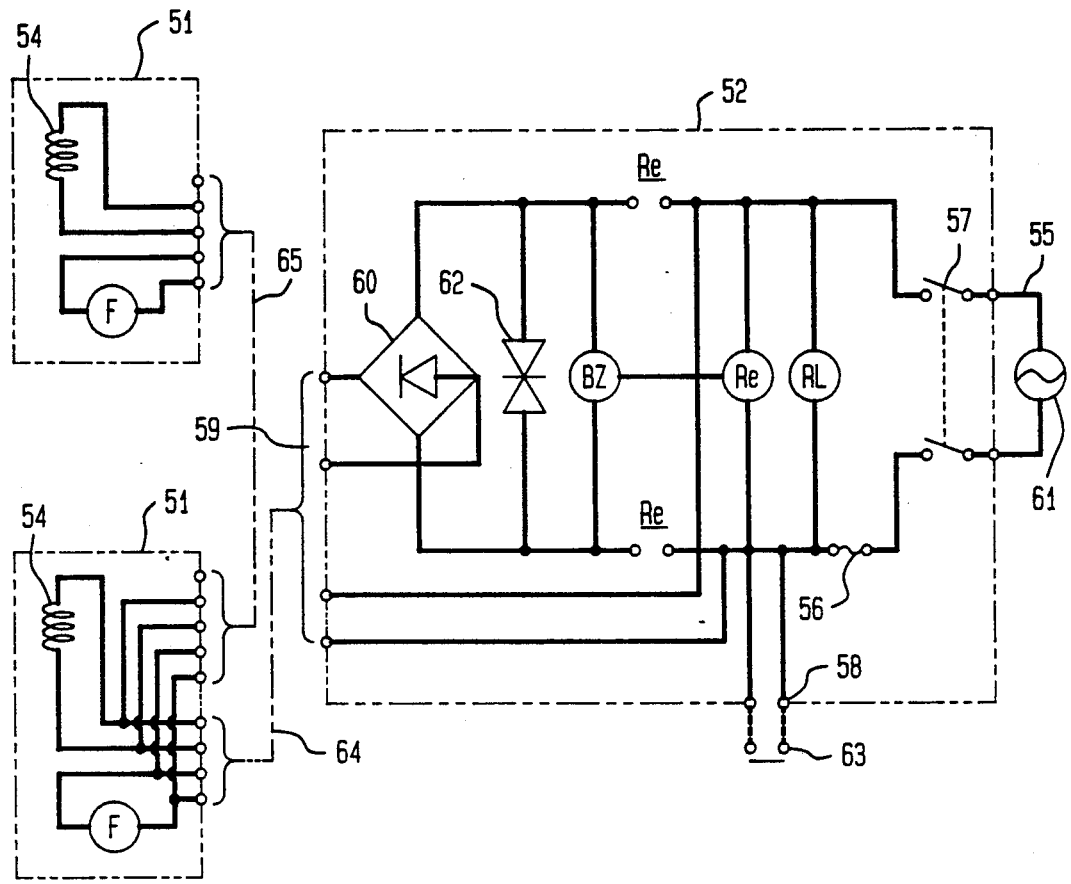
FIG. 5 is a circuit diagram showing the construction of a circuit incorporated in the embodiment shown in FIG. 4.

The construction of the electric current control unit 51 will be described with reference to a circuit diagram shown in FIG. 5. The rectifier 60 is connected to both ends of the A.C. power supply 61. The start lamp RL, electromagnetic relay Re, buzzer BZ and a constant voltage element 62 are connected in parallel to the rectifier 60. The snap switch 57 is constructed so as to simultaneously connect and disconnect both terminals of the A.C. power supply 61. The fuse 56, which is adapted to be molten in response to an over current in the main circuit, is connected in series to one of the terminals of the snap switch 57. A connector 58 for connecting the operation switch is connected in series to the electromagnetic relay Re. The operation switch 63 which is of a push-button type as shown in FIG. 4, is connected to the connector 58. In operation, therefore, the start lamp RL lights up as the starting snap switch 57 is turned on and, as the operation switch 63 is turned on, the electromagnetic relay Re is energized so that the rectifier 60 commences to rectify the A,C, current from the source 61 into D.C. current, while the buzzer BZ goes off.

A connection cord 64 is adapted to be connected to the D.C. power supply connector 59. The fans F in the magnetic field generating units 51 are driven by the A.C. power supply 61. The D.C. power and the A.C. power supplied to one of the magnetic field generating units are supplied to the other magnetic field generating unit 51 through connecting cords 65.

The operation of the medical capsule and actuating apparatus of the invention will be described hereinunder.

Figure 6:
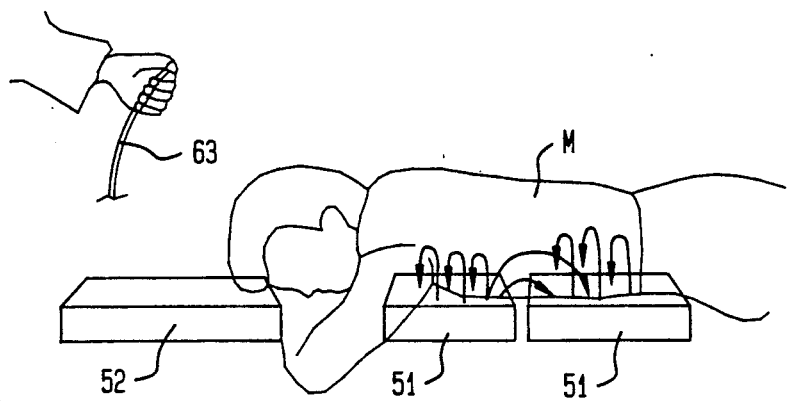
FIG. 6 is a schematic illustration showing the embodiment shown in FIG. 4 in a state for use.

The medical capsule for dosage of a medicine, set up in the manner illustrated in FIG. 1, is swallowed by a patient. The position of the capsule 1 inside the patient's body is traced and monitored by an external monitoring device such as an X-ray transmissive camera. When the capsule has reached a predetermined position inside the patient's body, the body M is moved to a position near the magnetic field generating units 51 as shown in FIG. 6. As the start switch 57 and the operation switch 63 of the actuating apparatus 50 are turned on, D.C. power and A.C. power are supplied to the magnetic field generating units 51, so that the fans F are started and the coils 54 are energized to generate magnetic fields between both ends of each of the coils 54. The duration of the period in which the operation switch 63 is held on may be as short as about 5 to 10 seconds. At the same time, magnetic fields are generated from N to S poles of both coils in the region between the two coils 54. Therefore, when the actuating apparatus is operated with the magnetic field generating units 51, 51 held in side-by-side fashion, magnetic lines of force are generated in various directions so as to to form magnetic fields over a wide area.

An experiment showed that the magnetomotive force of the magnetic field generating unit 51 is from 14000 to 15000 AT, and that the effective actuating distance between the magnetic field generating unit 51 and the capsule 1 is 30 cm when the magnetic field penetrates water and 20 cm when the magnetic field penetrates the living body. Thus, the magnetic lines of force generated from the magnetic field generating unit 51 are directed in all directions so that the lead switch s in the medical capsule 1 can be operated without fail regardless of the orientation of the capsule 1 in the body M, without requiring any further movement of the body M or of the unit 51.

Thus, the contacts 13 and 15 of the normally opened lead switches s in the capsule 1 inside the patient's body M are brought into contact to close the circuit by the magnetic fields generated by the magnetic field generating units 51. Until these contacts 13 and 15 contact each other, the current from the battery B does not flow so that wasteful use of the battery power is prevented.

As a result of the closing of the circuit by the contacts 13, 15, electrical current is supplied to the filament 16 to red-heat the same, so that the fixing thread 28 fixing the piston 5 is molten and cut. Consequently, the piston 5 moves to the left as viewed in the drawings by the force of the coiled spring 26. In an initial period of the movement t of the piston 5, the ports 9 in the outer cylinder 2 and the ports 10 in the piston 5 partially overlap each other, so that the working chamber A is communicated with the exterior so as to allow a fluid such as humor to flow into the working chamber A through the ports 9 and 10. In the case where the ports 9 and 10 are not provided, the pressurized air confined in the battery chamber C cancels the negative back pressure behind the piston 5, thus ensuring a smooth operation of the piston.

The medicine in the medicine chamber is pressurized in the beginning period of movement of the piston 5. This pressure, however, is absorbed by an elastic deformation of the seal film m and, hence, does not produce any undesirable effect.

Figure 3:
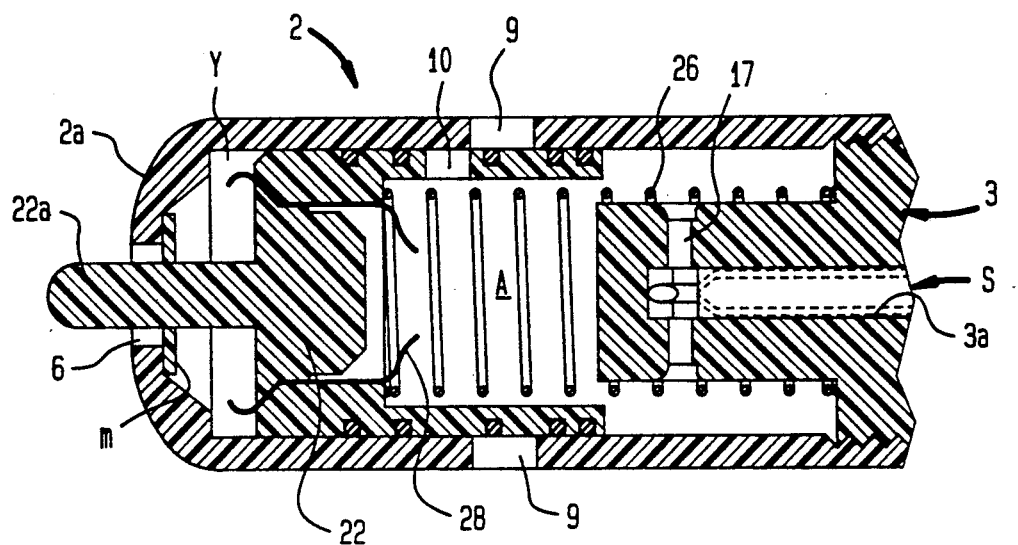
FIG. 3 is a sectional view illustrative of the operation of the embodiment shown in FIG. 1.

A further movement of the piston 5 causes the projection 22a on the piston 5 to break the seal film m as shown in FIG. 3, so that the whole of the medicine in the medicine chamber Y is discharged to the outside. Almost no portion of the medicine remains in the capsule because the spring continues to press the piston 5 even after the overlap of the ports 9 and 10 is ceased or even after the pressure of the compressed air has been reduced.

The capsule 1 after the dosage further moves in the patient's body and is discharge together with the human waste.

Figure 7:
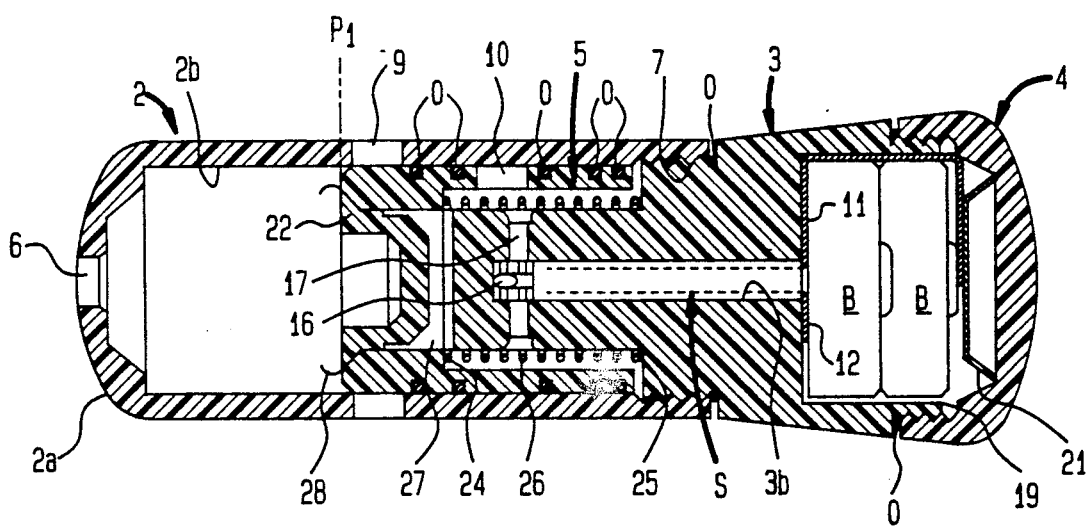
FIG. 7 is a sectional view of a second embodiment of the present invention.

FIG. 7 shows a second embodiment of the medical capsule intended for use as a sampling capsule 1a. In this Figure, the same reference numerals are used to denote the same parts to members as those appearing in FIGS. 1 to 3.

In this medical capsule 1a intended for use in sampling, the outer cylinder 2 has a substantially cylindrical inner wall 2b. The main block 3 is screwed to a threaded portion 7 formed on the open end of the outer cylinder 2, through an "O" rings o placed therebetween. First ports 9 are formed in the central portions of the wall of the outer cylinder 2. In the illustrated embodiment, four such first ports 1 are provided. This number of the ports 9, however, is only illustrative and any suitable number of ports 9 may be used provided that the number is the same as the number of second ports 10 formed in portions of the wall of the piston 5 so as to be brought into communication with the ports 9 when the piston 5 is moved in a manner explained later. When the capsule 1a is used for the sampling purpose, the liquid to be sampled, e.g., a humor, is sucked through the ports 9 and 10 and then stored in a sample chamber 27 which is defined by the inner peripheral surface of the piston 5 and the main block 3. Namely, when the piston 5 moves from a position P1 shown in FIG. 7 to a position P2 shown in FIG. 8 and then to a position P3 shown in FIG. 9, the volume of the sample chamber 27 is progressively increased so that a negative pressure is established in this chamber, whereby the liquid such as a humor is sucked and stored in the sample chamber 27.

Figure 8:
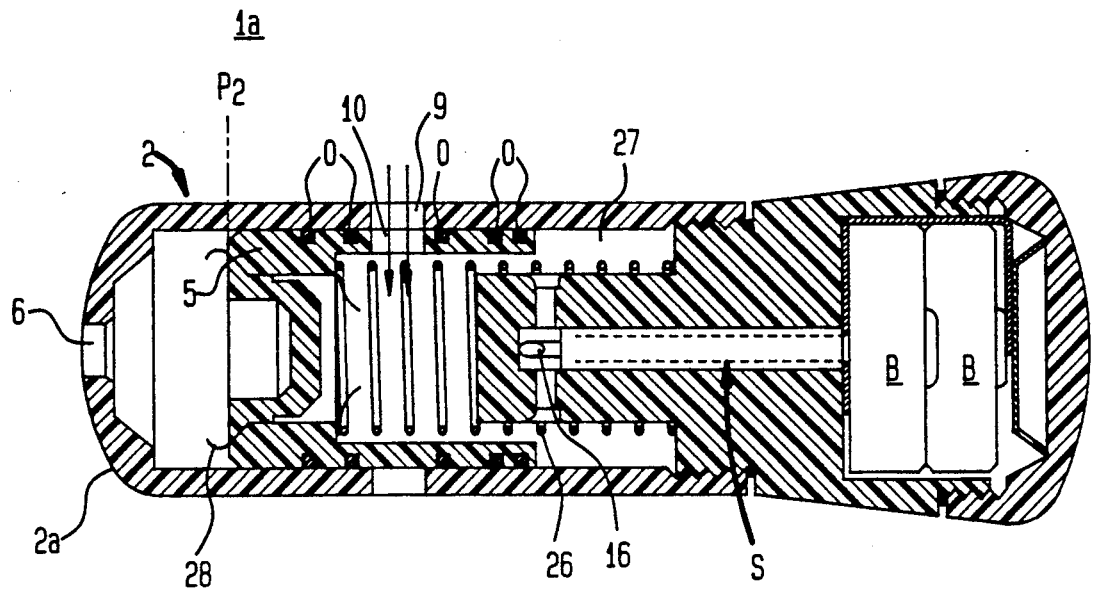
FIGS. 8 and 9 are sectional views of the second embodiment in different states of use.
Figure 9:
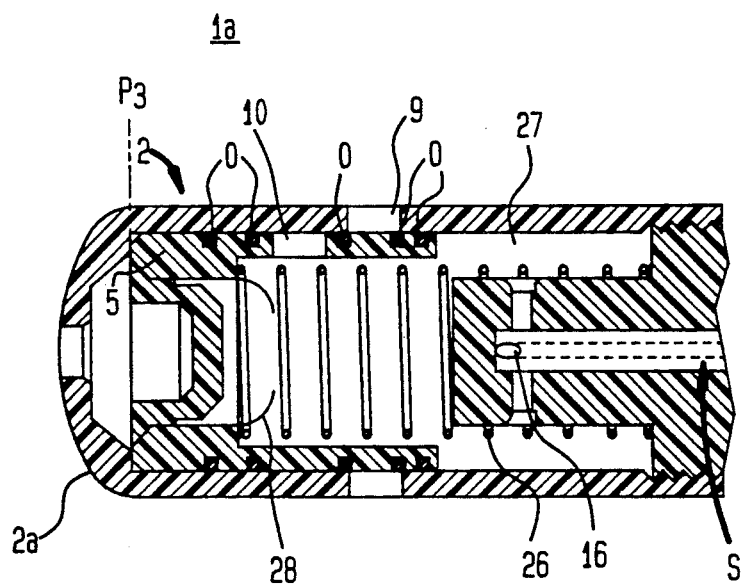
Figure 10:
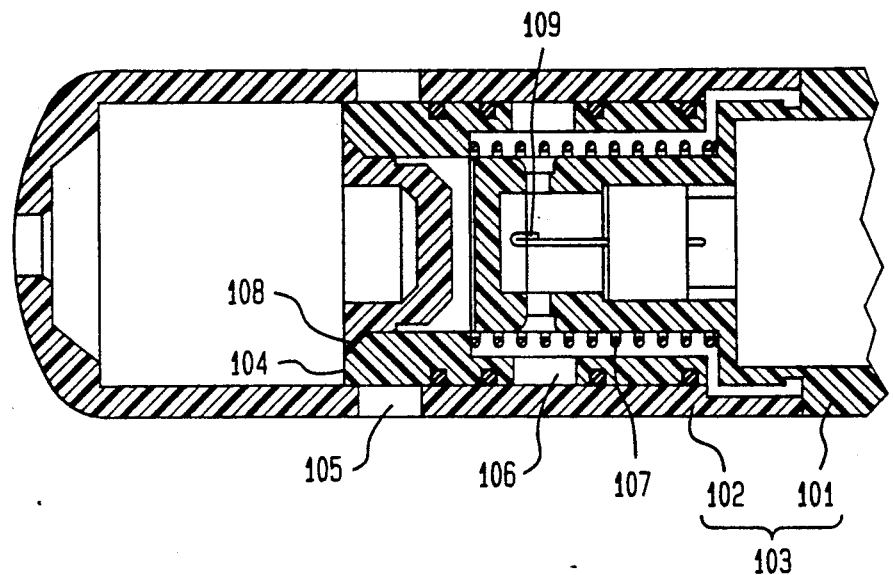
FIGS. 10 and 11 are illustrations of critical positions of known medical capsules.
Figure 11:
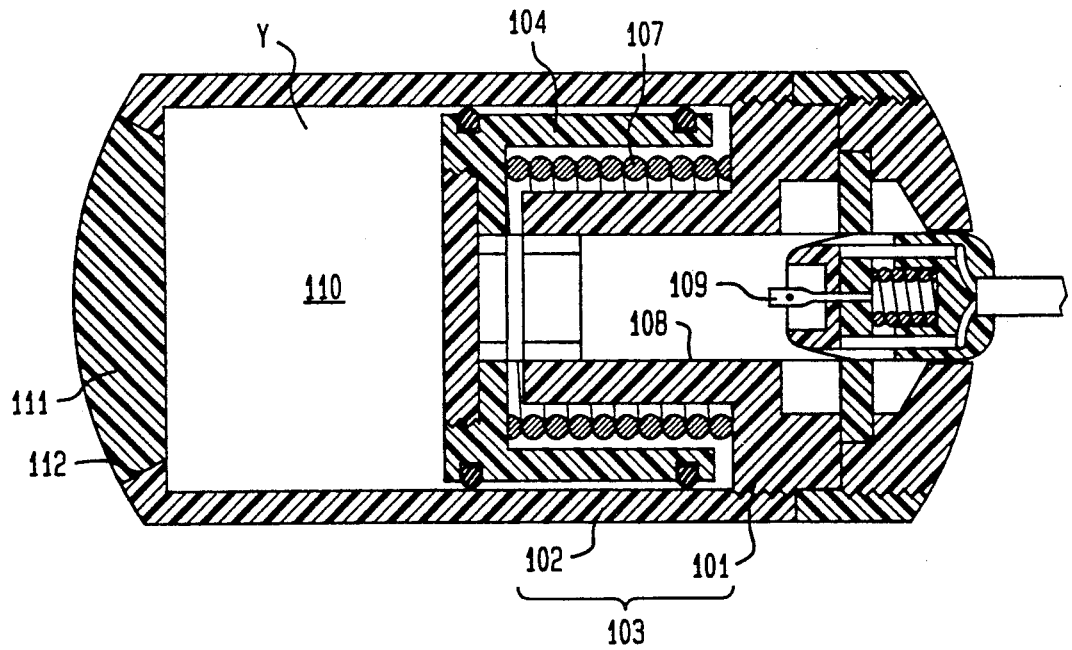

More specifically, as the fixing thread 28 is molten and cut by heat, the coiled spring 26 drives the piston 5 to the left as viewed in the Figure so that the first ports 9 in the outer cylinder 2 and the second ports 10 in the piston 5 tentatively overlap each other as shown in FIG. 8. In this state, since the gap between the piston 5 and the inner peripheral surface of the outer cylinder 2 is sealed by means of "O" rings o, a negative pressure has been established in the sample chamber 27 so that the fluid such a a humor is sucked through the first and second ports 9, 10 into the sample chamber 27 so as to be stored therein. A further leftward movement of the piston 5 by the force of the coiled spring 26 causes the sample chamber 27 to be sealed from the exterior of the capsule 1, whereby the sampled humor is confined and sealed in the sample chamber 27 as shown in FIG. 9.

The medical capsule 1a after the sampling is then discharged from the patient's body through the anus of the patient together with waste. The capsule 1a thus picked up is then decomposed to separate the outer cylinder 2 and the main block 3 from each other, so that the sampled humor is taken out for the purpose of diagnostic inspection.

Although two preferred embodiments have been described, it is to be understood that the described embodiments are only illustrative and various changes and modifications may be imparted thereto. For instance, the projection 22a in the dosing capsule 1 shown in FIG. 1 may be prolonged as indicated by broken line so that it can puncture the seal film m immediately after the start of movement of the piston. The projection 22a also may be provided with grooves in its peripheral surface so that the discharge of the medicine can be conducted without being restricted even when the seal film m has a comparatively high rigidity to fit around the projection 22a after the puncture. Although polytetrafluoroethylene is mentioned as a preferred material of the seal film m, this material may be substituted by a thin rubber film stiffened by a starch-type paste.

Furthermore, although capsules 1 and 1a for dosage and sampling have been described independently as first and second embodiments, it is possible to construct a single medical capsule which can simultaneously perform both dosage and sampling.

What is claimed is:

1. A capsule for medical use to be swallowed by a patient comprising:
    a main block having a first and second end;
    an outer cylinder mounted on said first end of said main block, said outer cylinder having a discharge opening extending through an end portion thereof;
    a cover surrounding said second end of said main block;
    a film seal positioned over said discharge opening;
    a chamber formed between said main block, said seal and said outer cylinder;
    a piston positioned in said chamber, said piston having a projection positioned above said film seal;
    biasing means connected to said piston and said main block for exerting a biasing force on said piston for slidably moving said piston towards said film seal so that said projection is propelled against said film seal for puncturing said film seal;
    a fixing thread attached to said piston for releasably retaining said piston against said biasing force exerted by said biasing means;
    a filament for heating said thread to melt-cut said thread thereby releasing said piston when said filament is actuated; and
    switching means adapted to be remotely turned on when said capsule has reached a predetermined position in the patient's body as a result of an externally applied magnetic field, said switching means including a pair of contacts formed of a resilient magnetic material and a power means, said filament being actuated by supplying power from said power means to said filament, thereby releasing any substance contained in said chamber through said discharge opening in said cylinder.

2. The capsule according to claim 1 wherein said outer cylinder includes at least one port on the side walls thereof whereby when said biasing means slidably moves said piston a sample to be collected flows through said at least one port into the portion or said chamber positioned behind said piston.

3. The capsule according to claim 1 wherein said seal is formed of polytetrafluoroethylene.

4. The capsule according to claim 1 wherein a combustible material is applied to said fixing thread.

5. The capsule according to claim 4, wherein said fixing thread is provided so as to contact said filament in a cavity formed in said main lock.

6. The capsule according to claim 4, wherein said fixing thread is made of polyethylene terephthalate and is impregnated with a combustible oil.

7. The capsule according to claim 1, wherein said block, said outer cylinder and said cover are made from a polycarbonate resin.

8. The capsule according to claim 1 wherein said power means is a battery.

9. The capsule according to claim 8 wherein said battery is a silver battery.

* * * * *